(12) United States Patent
Volkmann

(10) Patent No.: US 7,670,606 B2
(45) Date of Patent: Mar. 2, 2010

(54) METHOD FOR ADMINISTERING A VAGINAL CARE COMPOSITION

(76) Inventor: Peter-Hansen Volkmann, Kücknitzer Hauptstrasse 53, D-23569 Lübeck (DE)

( * ) Notice: Subject to any disclaimer, the term of this patent is extended or adjusted under 35 U.S.C. 154(b) by 498 days.

(21) Appl. No.: 11/599,965

(22) Filed: Nov. 15, 2006

(65) Prior Publication Data

US 2007/0059298 A1    Mar. 15, 2007

Related U.S. Application Data

(62) Division of application No. 10/977,742, filed on Oct. 29, 2004, now abandoned.

(30) Foreign Application Priority Data

Nov. 3, 2003   (EP)   ................................. 03025152

(51) Int. Cl.
| | | |
|---|---|---|
| *A61K 39/38* | (2006.01) | |
| *A61K 45/00* | (2006.01) | |
| *A61F 13/02* | (2006.01) | |
| *A61F 13/00* | (2006.01) | |

(52) U.S. Cl. ................. 424/184.1; 424/278.1; 424/431; 424/434

(58) Field of Classification Search .................. None
See application file for complete search history.

(56) References Cited

U.S. PATENT DOCUMENTS

| 5,702,714 A * | 12/1997 | Goss ........................ 424/401 |
| 6,093,394 A | 7/2000 | Chrisope |
| 6,783,780 B1 * | 8/2004 | De Jong et al. ............... 426/52 |
| 2002/0015990 A1 * | 2/2002 | Tomita et al. ............. 435/253.6 |
| 2002/0045242 A1 | 4/2002 | Hata et al. |
| 2003/0003107 A1 * | 1/2003 | Farmer .................... 424/184.1 |
| 2003/0003138 A1 | 1/2003 | Di Cintio et al. |
| 2005/0180962 A1 * | 8/2005 | Raz et al. ................. 424/93.45 |
| 2005/0226949 A1 * | 10/2005 | Bland et al. .................. 424/757 |
| 2006/0018986 A1 * | 1/2006 | Breton ....................... 424/776 |
| 2006/0057132 A1 * | 3/2006 | De Simone .............. 424/93.45 |

FOREIGN PATENT DOCUMENTS

| BR | 200002018 | | 1/2002 |
| EP | 001118340 | | 7/2001 |
| PT | RPI1617 | | 1/2002 |
| WO | WO 92/13577 | * | 8/1992 |
| WO | WO 03/071883 | | 9/2003 |
| WO | WO 03/080813 | | 10/2003 |
| WO | WO03/082306 | | 10/2003 |

OTHER PUBLICATIONS

Austrian Search Report.
Elmer et al., "Biotherapeutic Agents, A neglected modality for the treatment and prevention . . . ", JAMA, 1996, 275, (11), pp. 870-876. (OA) (willfollow).
Melaleuca oil nomenclature, http://goldpharma.info/4669-f.htm., pp. 1-3 (OA).

* cited by examiner

*Primary Examiner*—Robert B Mondesi
*Assistant Examiner*—Lakia J Tongue
(74) *Attorney, Agent, or Firm*—Collard & Roe, PC

(57) ABSTRACT

A vaginal care composition is introduced directly into the vagina in the form of an ovule, a cream or an ointment or with a tampon or which is brought into a position outside the vagina on a panty liner. The composition comprises viable *Lactobacillus* or *Bifidobacterium* microorganisms, non-viable *Saccharomyces* cultures, saccharide(s), vitamin A, and zinc.

27 Claims, No Drawings

METHOD FOR ADMINISTERING A VAGINAL CARE COMPOSITION

CROSS-REFERENCE TO RELATED APPLICATIONS

This application is a divisional of U.S. patent application Ser. No. 10/977,742, filed on Oct. 29, 2004 now abandoned.

BACKGROUND OF THE INVENTION

The present invention relates to a method of applying a vaginal care composition. In particular, the invention relates to a vaginal care composition which is introduced directly into the vagina in the form of an ovule, a cream or an ointment or with a tampon or which is brought into a position outside the vagina on a panty liner.

It has long been known that mucosae can be very sensitive. The mucosa of the vagina is particularly sensitive to irritations or inflammations. Women who are so predisposed react, for example after visiting a swimming pool or other body of water or after sexual intercourse, with irritations, painful changes or even inflammation in the region of the vaginal mucosa. Hormonal changes, for example when taking the pill ("contraceptive pill"), in pregnancy, lactation or during the menopause, can also cause an irritated reaction in the vaginal mucosa. Similarly, systemic treatment with antibiotics, for example, also causes irritations of the mucosae, in particular the vaginal mucosa. A further irritating factor for the vaginal flora is the increasing discharge from the vagina, which originally comes from the abdominal cavity and, owing to an unphysiological composition of the secretions, can disturb the normal balance of the vaginal population.

The resulting irritations of the vaginal mucosa are not only painful but can also develop into advancing inflammations, which can affect other organs or the woman's entire body. In fact, several hundred thousand women are affected each year by such irritations, which can impair their feeling of well-being considerably.

One theory which might explain why irritations and inflammatory reactions can develop involves the formation of biofilms. Such biofilms may be involved in the formation of/colonization with pathogenic microorganisms and/or affect them in a supporting manner or even inhibit them. It would therefore be desirable to prevent such pathological biofilms from developing. The formation of a physiological mucosa-protecting film is the aim of this application.

Accordingly, the mucosa should be cared for in such a manner that it is better able to withstand environmental influences and does not offer an environment in which pathological biofilms are able to develop. Such care has already been widely practiced for a long time, for example for the outer skin of the body, for example by the use of caring oils or creams, preferably on a regular basis, but in particular after the skin has been exposed to particular stresses, for example after sunbathing or after showering or swimming.

For protection against infections when visiting swimming pools, there are tampons which are intended to prevent such infections. These "Symbiofem" tampons, which are to be found, for example, on the website www.symbiofem.com, are impregnated with Vaseline oil. However, these tampons provide only a purely mechanical barrier layer which does not contribute to caring for the vaginal mucosa in any way. On the contrary, it is questionable whether contact with highly concentrated Vaseline oil is beneficial to the mucosal environment. Furthermore, the Vaseline oil prevents a tampon from expanding in the required manner, so that it is barely able to adapt exactly to the body shape of the wearer and, in the end, water will nevertheless be allowed through.

Care products for the vaginal mucosa, with which the mucosa can be similarly cared for and protected, are therefore desirable.

SUMMARY OF THE INVENTION

Accordingly, the object of the present invention is to provide a vaginal care composition with which the mucosa of the vagina can be protected.

The invention comprises a vaginal care composition comprising viable *Lactobacillus* and/or *Bifidobacterium* microorganisms, preferably *Lactobacillus bifidus*; non-viable *Saccharomyces* cultures, preferably *Saccharomyces cerevisiae*; saccharide(s); vitamin A/retinol, and zinc.

*Lactobacillus* is the microorganism that is preferably used. It is preferably selected from the group consisting of: *Lactobacillus bifidus, Lactobacillus rhamnosus, Lactobacillus acidophilus, Lactobacillus crispatus, Lactobacillus fermentum, Lactobacillus plantarum, Lactobacillus casei, Lactobacillus paracasei, Lactobacillus jensenii, Lactobacillus gasseri, Lactobacillus cellobiosis, Lactobacillus brevis, Lactobacillus delbrueckii, Lactobacillus rogosae* and *Lactobacillus bifidum*.

It is also possible to use *Bifidobacterium* alone or in admixture with the above *Lactobacillus*. It is preferably selected from: *Bifidobacterium bifidum, Bifidobacterium breve, Bifidobacterium adolescentis* or *Bifidobacterium longum*.

The above species can be used alone or in the form of a mixture of two or more species. Preferably, the microorganisms are present in the composition in lyophilised or heat-dried form. In any case, they must be present in the composition in a viable manner which allows them to grow and multiply on contact with moisture (which originates, for example, from the vaginal environment).

The preferred *Saccharomyces* species is *Saccharomyces cerevisiae*. This is present in the composition in the form of a culture, e.g. in dried form. The *Saccharomyces* culture must not be viable, so that it does not compete with *Lactobacillus* or *Bifidobacterium*; it serves as the starting material for the growth of the *Lactobacilli/Bifidobacteria* and as the nutrient medium for their further multiplication.

One embodiment of composition additionally comprises selenium, especially selenium-containing yeast, preferably in an amount of from 0.001 to 0.06 wt. % selenium. Selenium is an antioxidant trace element with cell-protecting properties, which particularly promotes the growth of *Lactobacilli and Bifidobacteria* and therefore furthers their development over other microorganisms in the vagina.

Another embodiment additionally comprises *Melaleuca aetheroleum*, preferably in an amount of from 0.5 to 10 wt. %, and/or camomile flower extract, preferably in an amount of from 0.01 to 5 wt. %. Both substances assist in the care of the vaginal mucosa by their inflammation-relieving and caring properties.

In a particularly preferred embodiment, the vaginal care composition additionally comprises D-alpha-tocopherol, preferably in an amount of from 0.5 to 5 wt. %, and/or pantothenate, preferably in an amount of from 0.1 to 3 wt. %. According to a preferred embodiment, tocopherol acts as an antioxidant for oils introduced by the composition and also as cell protection for skin and mucosa. Pantothenate is a vitamin which again promotes the growth of Lactobacilli and/or *Bifidobacterium* over other microorganisms and (so) contributes particularly to the care of the vaginal mucosa owing to its properties as a vitamin.

According to a further preferred embodiment, the vaginal care composition additionally comprises fragrances, preferably natural fragrances, particularly preferably lavender oil in an amount of from 0.5 to 10 wt. %. The fragrances may be present, for example, in order to make the care composition more acceptable to a potential user.

The vaginal care composition may comprise cocoa butter or a hard-fat carrier, for example, as the base. Such carriers are known to the person skilled in the art. They are distinguished in particular by their good tolerability in the region of the vagina and do not give rise to irritations or possible allergic reactions there.

A vaginal care composition is described by way of example hereinbelow, which composition comprises constituents in the following amounts (in the following, wt. % are always based on the total composition):

Lactobacillus/Bifidobacterium: from $10^7$ to $10^{10}$ microorganisms/g, from 3 to 5% composition
Saccharomyces: from 0.1 to 40 wt. %
saccharide(s): from 1 to 40 wt. %
vitamin A: from 0.01 to 0.5 wt. %
zinc: from 0.2 to 10 wt. %.

The saccharide for the vaginal care composition is preferably selected from: oligofructose, inulin and/or lactose, preference being given to oligofructose. It is also possible to use a mixture of two or more of the above-mentioned saccharides. The saccharides serve especially as starting materials for the development of the Lactobacilli and Bifidobacteria. These utilize the saccharides and as a result have a growth advantage over other microorganisms.

The vaginal care composition may be so composed that the zinc is used in the form of zinc sulfate and/or zinc gluconate. The vaginal care composition may also have a formulation in which the vitamin A is used in the form of retinyl acetate and/or retinyl gluconate. These forms of addition of zinc and vitamin A are known to the person skilled in the art. Other forms of zinc and vitamin A can be chosen, provided that the function of the composition as a care composition for the vaginal mucosa is not impaired thereby.

Depending on its type, the composition may also comprise further conventional constituents, provided that they do not impair the function of a care composition. Such constituents may be selected, for example, from binders, excipients, solvents, stabilizers, lubricants, disintegrators and carriers, such as, for example, solid or liquid carriers.

According to a main aspect of the present invention, the vaginal care composition as defined above is used for the care of the vaginal mucosa and/or for preventing infections thereof by bacteria, fungi and/or viruses. The particular composition allows the vaginal mucosa to be cared for without being adversely affected or impaired. This care can take place on a regular basis or as required, for example in phases of hormonal change, such as, for example, during pregnancy, during lactation, in the menopause or post-menopausal. It is also possible to care for the mucosa in a very targeted manner, for example before and/or after visiting public bodies of water, such as, for example, bathing pools or swimming baths.

The vaginal care composition is preferably applied directly to the vaginal mucosa. This can be effected, for example, by introducing the composition into the vagina in the form of an ovule or a cream or ointment and thereby bringing it into direct contact with the mucosa. It is also possible for the composition to be contained in a tampon which is then inserted into the vagina, the composition thereby coming into contact with the mucosa. Finally, according to a further preferred embodiment, the composition is contained in a panty liner. The composition is in each case activated by moisture, for example the moisture of the usual vaginal environment. "Activation" in this context means that the Lactobacilli and/or Bifidobacteria contained therein begin to grow and multiply.

According to a particularly preferred embodiment, therefore, the present invention relates to a caring ovule comprising the vaginal care composition as defined above. The caring ovule having a weight of from 2 to 5 g, preferably 3 g, per ovule, preferably comprises the following per gram:

from $10^7$ to $10^9$, preferably $10^8$, microorganisms/g, 5% Lactobacillus bifidus
from 1 to 10 wt. %, preferably 2.5 wt. %, Saccharomyces cerevisiae,
from 0.05 to 0.3 wt. %, preferably 0.1 wt. %, vitamin A,
from 1 to 3 wt. %, preferably 1.8 wt. %, -alpha-tocopherol,
from 0.4 to 1.5 wt. %, preferably 0.9 wt. %, pantothenate,
from 0.5 to 5 wt. %, preferably 0.8 wt. %, zinc,
from 0.002 to 0.02 wt. %, preferably 0.005 wt. %, selenium,
from 1 to 5 wt. %, preferably 3 wt. %, Melaleuca aetheroleum,
from 1 to 5 wt. %, preferably 3 wt. %, lavender oil,
from 0.2 to 3 wt. %, preferably 1 wt. %, camomile flower oil extract and/or
from 2 to 20 wt. %, preferably 5 wt. %, oligofructose.

DETAILED DESCRIPTION OF THE PREFERRED EMBODIMENT

The preferred composition of an ovule is summarized hereinbelow in table form, the combinatory action being indicated in each case:

TABLE 1

Formulation for 3 g vaginal ovules with Adeps solidus

| Substance | Microorganisms/g/ wt. % | Formulation wt. % | Content of pure substance | Action in the combination |
|---|---|---|---|---|
| Lactobacillus bif. | microorganisms/g | $10^8$/g 10 | 300 mg | Repopulation or control of the vaginal flora |
| Saccharomyces cer. | wt. % | 2.5 | 75 mg | Nutrient medium for symbionts and vitamin B pool |
| Retinol acetate | wt. % | 0.1 | Vit. A 3 mg | Care of mucosa and healing of wounds |
| α-Tocopherol acet. | wt. % | 1.8 | Vit. E 54 mg | Antioxidant, care of mucosa and healing of wounds in microtraumas |
| (Ca) pantothenate | wt. % | 0.9 | B5 27 mg | Care of mucosa and healing of wounds in microtraumas |
| Zinc (sulfate) | wt. % | 0.8 | Zn 24 mg | Skin protection against Candida |
| Selenium as yeast | wt. % | 0.005 | Se 150 μg | Antioxidant with cell-protecting |

TABLE 1-continued

Formulation for 3 g vaginal ovules with Adeps solidus

| Substance | Microorganisms/g/ wt. % | Formulation wt. % | Content of pure substance | Action in the combination |
|---|---|---|---|---|
| | | | | functions |
| *Melaleuca aetherol.* | wt. % | 3 | 90 mg | Care oil for mucosa |
| *Camomile* flower oil extract | wt. % | 1 | 30 mg | Care of mucosa |
| Lavender oil | wt. % | 3 | 90 mg | Fragrance and care oil |
| Oligofructose | wt. % | 5 | 150 mg | Starter for Lactobacilli and saccharide-degrading symbionts present |

Within the scope of the present invention, the term "ovule" is to include the solid forms, such as, for example, vaginal suppositories, for insertion into the vagina that are known by this name to the person skilled in the art, as well as foaming tablets or depot implants. An ovule preferably comprises the conventional bases, such as, for example, Whitepsol, Massa Estarinum, coconut fat, glycerol-gelatin compositions, glycerol soaps or polyethylene glycol. According to a further preferred embodiment, the present invention relates to a care cream comprising the vaginal composition as defined above. The care cream preferably comprises from $10^7$ to $10^9$, preferably $10^8$, microorganisms/g *Lactobacillus bifidus*, 5%, from 1 to 10 wt. %, preferably 2.5 wt. %, *Saccharomyces cerevisiae*, from 0.05 to 0.3 wt. %, preferably 0.1 wt. %, vitamin A, from 1 to 3 wt. %, preferably 1.5 wt. %, D-alpha-tocopherol, from 0.4 to 1.5 wt. %, preferably 0.7 wt. %, pantothenate, from 1 to 6 wt. %, preferably 3 wt. %, zinc, from 1 to 5 wt. %, preferably 2 wt. %, *Melaleuca aetheroleum*, from 0.05 to 3 wt. %, preferably 1 wt. %, camomile flower extract, from 2 to 20 wt. %, preferably 5 wt. %, oligofructose and/or from 1 to 5 wt. %, preferably 3 wt. %, lavender oil.

According to a further preferred form, the care cream comprises further conventional cream or ointment constituents, especially constituents selected from the following group: sunflower oil, Tegomuls 90 S, cetyl alcohol, Cetaceum artificiale, Polysorbat 80, methyl 4-hydroxybenzoate, propyl 4-hydroxybenzoate, sesame oil, wool wax, yellow wax, wool wax alcohols, glycerol, glycerol esters, palmitic acid ester, white Vaseline, liquid wax, olive oil and/or distilled water.

The term "cream" within the scope of the present invention includes creams, ointments, as well as emulsions, and liquid compositions to be released from gelatin.

A particularly preferred ointment base is the following:

sunflower oil, Tegomuls 90 S, cetyl alcohol, Cetaceum artificiale, Polysorbat 80, methyl 4-hydroxybenzoate and propyl 5-hydroxybenzoate in distilled water, or sesame oil, wool wax, yellow wax, wool wax alcohols, or glycerol, glycerol ester, palmitic acid ester, white Vaseline, liquid wax, or yellow wax, olive oil.

According to a another embodiment, the invention relates to a caring vaginal tampon comprising the vaginal care composition as defined above. Particularly preferably, the caring vaginal tampon may comprise the following (comprising from 2 to 5 g, preferably 3 g, of the vaginal care composition per tampon) (per gram of composition):

from $10^7$ to $10^9$, preferably $10^8$, microorganisms/g *Lactobacillus bifidus*, 5%, from 1 to 10 wt. %, preferably 2.5 wt. %, *Saccharomyces cerevisiae*, from 0.05 to 0.3 wt. %, preferably 0.1 wt. %, retinol acetate, from 1 to 3 wt. %, preferably 1.5 wt. %, D-alpha-tocopherol, from 1 to 6 wt. %, preferably 0.8 wt. %, zinc, from 1 to 5 wt. %, preferably 2 wt. %, *Melaleuca aetheroleum* and/or from 2 to 20 wt. %, preferably 3 wt. %, oligofructose.

In order that the composition can reach the vaginal mucosa as easily and quickly as possible, the caring vaginal tampon should contain the vaginal care composition on a superficial layer of the tampon, the composition being applied by spraying or immersion processes, for example. Optionally, the composition may also penetrate the entire tampon. According to a particularly preferred embodiment, the vaginal care composition can also be contained solely in a layer directly beneath the outer cover layer of the tampon.

The vaginal care composition of the present invention can be applied to any tampon known to the person skilled in the art or such a tampon can be impregnated with the composition. For example, the tampon consists of a form twisted in on itself, with grooves or indentations directed outwardly, i.e. towards the body of the wearer, which facilitate the passage of liquid into the inside of the tampon. The tampon preferably further has an outer, liquid-repelling layer and an inner liquid-storing layer. It advantageously also contains materials that swell in liquid, so that the tampon is able to adapt to the body shape of the particular wearer. For example, the tampon may have a cover layer comprising cellulose which swells on contact with liquid and without delay forms a gel, which facilitates insertion. Such a tampon is known to the person skilled in the art.

According to another embodiment, the vaginal care composition according to the present invention is contained in an outer layer of the tampon, without the invention being limited thereto.

According to a further embodiment, the invention relates to a caring panty liner comprising the vaginal care composition as defined above. Preferably, the caring panty liner, which comprises from 2 to 4 g, preferably 3 g, of the vaginal care composition per panty liner, comprises in 1 g of the composition:

from $10^7$ to $10^9$, preferably $10^8$, microorganisms/g *Lactobacillus bifidus*, 5%, from 1 to 10 wt. %, preferably 2.5 wt. %, *Saccharomyces cerevisiae*, from 0.05 to 0.3 wt. %, preferably 0.1 wt. %, retinol acetate, from 1 to 3 wt. %, preferably 1.5 wt. %, D-alpha-tocopherol, from 1 to 6 wt. %, preferably 3 wt. %, zinc and/or from 2 to 20 wt. %, preferably 3 wt. %, oligofructose.

The caring panty liner can contain the vaginal care composition on an upper layer, preferably applied by a spraying process. It is also possible to form the caring panty liner in such a manner that the vaginal care composition is contained solely in a layer directly beneath the cover layer of the panty liner.

The vaginal care composition can be applied to/introduced onto any panty liner known to the person skilled in the art. For example, the panty liner may consist of a moisture-permeable cover layer, a moisture-repelling layer arranged beneath it, a moisture-storing layer arranged beneath the moisture-repelling layer, and a backing layer that is impermeable to liquid. The cover layer may have pores, for example, which facilitate the drawing off of liquid and improve aeration. Masking substances which improve the appearance of the panty liner may also be present. The vaginal care composition of the present invention is particularly preferably contained in a layer beneath the cover layer, without the invention being limited thereto.

In a further embodiment, the present care composition of the invention can also be used as a urethra stick for caring for the urethral mucosa in the case of partner care for men. The care composition in this embodiment may be embedded, for example, in a urethra stick of Adeps solidus. This stick should have a length of from 10 to 30 cm, preferably 25 cm, and a diameter of from 2.5 to 7 mm, preferably 4.5 mm. It can be broken into segments by means of predetermined breaking points, which are arranged, for example, at intervals of about 5 cm.

A preferred composition for the urethra stick consists of *Lactobacillus bifidus* microorganisms, with *Saccharomyces cerevisiae* and oligofructose as starter. Vitamin A, alpha-tocopherol, pantothenate, zinc, selenium, *Melaleuca aetheroleum* and fragrances should also be present. Preferably, the urethra stick comprises, per gram:

from $10^7$ to $10^9$, preferably $10^8$, *Lactobacillus bifidus* microorganisms, from 1 to 10 wt. %, preferably 2.5 wt. %, *Saccharomyces cerevisiae*, from 0.05 to 0.3 wt. %, preferably 0.1 wt. %, retinol acetate, from 1 to 3 wt. %, preferably 1.5 wt. %, D-alpha-tocopherol, from 1 to 6 wt. %, preferably 3 wt. %, zinc and/or from 2 to 20 wt. %, preferably 3 wt. %, oligofructose.

The dosage of the vaginal care composition according to the invention is dependent on factors known to the person skilled in the art; care of the mucosa is usually to be carried out from 1 to 3 times daily using up to 3 g of the composition; alternatively, immediately before and after particular stress, such as swimming or sexual intercourse. Long-term care can be carried out using, for example, 6 ovules per cycle.

EXAMPLES

1. Ointment

A. Preparation, composition

An ointment having the following composition was prepared:

$10^8$ microorganisms/g *Lactobacillus bifidus* (/g) to form 10% of the composition according to the invention 2.5 wt. % *Saccharomyces cerevisiae*, as nutrient medium 0.1 wt. % retinyl acetate 1.8 wt. % D-alpha-tocopherol 0.9 wt. % pantothenate 0.8 wt. % zinc 0.005 wt. % selenium (as selenium-containing yeast)

3 wt. % *Melaleuca aetheroleum*

1 wt. % camomile flower extract 3 wt. % lavender oil 5 wt. % oligofructose mixed according to the processes known to the person skilled in the art for the preparation of ointments in a mixture of yellow wax and olive oil.

B. Application

A woman (25 years old, taking the pill) who in the past 5 years had suffered several vaginal mycoses, in each case in the summer, used the above ointment according to the following directions:

Once daily, in the evening, 3 g of the ointment were distributed over the vaginal mucosa. Care was begun in May. During the following summer months, no mycoses occurred.

2. Ovule

A. Preparation, composition

Each ovule weighed 3 g and was prepared from the following mixture according to the processes known to the person skilled in the art for the preparation of ovules:

$10^8$ *Lactobacillus bifidus* microorganisms/g, 5% of the composition according to the invention 2.5 wt. % *Saccharomyces cerevisiae*, as a culture 0.1 wt. % retinyl acetate 1.5 wt. % D-alpha-tocopherol 0.7 wt. % pantothenate 0.8 wt. % zinc 0.005 wt. % selenium (as selenium-containing yeast)

2 wt. % *Melaleuca aetheroleum*

1 wt. % camomile flower extract 3 wt. % lavender oil 3 wt. % oligofructose the ingredients were mixed into Adeps solidus having a melting point of 34.5 degrees Celsius.

B. Application

A woman (43 years old) who in previous years had suffered about 3 to 5 vaginal mycoses per year used the ovules, starting in January, according to the following directions: An ovule is inserted once daily, in the evening.

Thereafter she was free of vaginal infections for the remainder of the year.

The above Examples and the description are intended to illustrate the invention further without limiting the scope thereof, which is defined by the claims.

What is claimed is:

1. A method of caring for the vaginal mucosa, comprising administering an effective amount of a composition comprising viable *Lactobacillus bifidus*, non-viable *Saccharomyces cerevisiae*, D-alpha-tocopherol, pantothenate, zinc, selenium, and oligofructose.

2. The method according to claim 1, wherein the composition is applied directly to the vaginal mucosa.

3. The method according to claim 1, wherein the selenium includes yeast having from 0.001 to 0.06 wt. % selenium.

4. The method according to claim 1, wherein the composition additionally comprises fragrances.

5. The method according to claim 1, wherein the composition further comprises cocoa butter or a hard-fat carrier as a base.

6. The method according to claim 1, wherein the zinc is in the form of zinc sulfate or zinc gluconate.

7. The method according to claim 1, wherein the composition further comprises retinyl acetate, *melaleuca aetheroleum*, camomile flower extract and lavender oil.

8. The method according to claim 7, wherein the lavender oil is present in an amount of from 0.5 to 10 wt. %.

9. The method according to claim 1, wherein the composition is administered in the form of a care cream.

10. The method according to claim 9, wherein the care cream comprises:
from $10^7$ to $10^9$ *Lactobacillus bifidus* microorganisms/g,
from 1 to 10 wt. % *Saccharomyces cerevisiae*,
from 0.05 to 0.3 wt. % vitamin A,
from 1 to 3 wt. % D-alpha-tocopherol,
from 0.4 to 1.5 wt. % pantothenate,
from 1 to 6 wt. % zinc,
from 1 to 5 wt. % *Melaleuca aetheroleum*,
from 0.05 to 3 wt. % camomile flower extract,
from 2 to 20 wt. % oligofructose or from 1 to 5 wt. % lavender oil.

11. The method according to claim 9, wherein the care cream further comprises constituents selected from the following group: sunflower oil, Tegomuls 90 S, cetyl alcohol, Cetaceum artificiale, Polysorbat 80, methyl 4-hydroxybenzoate, propyl 4-hydroxybenzoate, sesame oil, wool wax, yellow wax, wool wax alcohols, glycerol, glycerol esters, palmitic acid ester, white Vaseline, liquid wax, olive oil and distilled water.

12. The method according to claim 1, wherein the composition is administered in the form of an ovule.

13. The method according to claim 12, wherein the ovule has a weight of 3 g, and a composition of the following:
from $10^7$ to $10^9$, Lactobacillus bifidus microorganisms/g,
from 1 to 10 wt. % *Saccharomyces cerevisiae*,
from 0.05 to 0.3 wt. % vitamin A,
from 1 to 3 wt. % D-alpha-tocopherol,
from 0.4 to 1.5 wt. % pantothenate,
from 0.5 to 5 wt. % zinc,
from 0.002 to 0.02 wt. % selenium,
from 1 to 5 wt. % *Melaleuca aetheroleum*,
from 1 to 5 wt. % lavender oil,
from 0.2 to 3 wt. % camomile flower oil extract, and
from 2 to 20 wt. % oligofructose.

14. The method according to claim 12, wherein the ovule is composed of coconut oil, glycerol-gelatin or polyethylene glycol.

15. The method according to claim 12, wherein the ovule further comprises cocoa butter or hard fats.

16. The method according to claim 1, wherein the composition is administered in the form of a panty liner.

17. The method according to claim 16, wherein the panty liner contains from 2 to 5 g of the composition and the composition comprises:
from $10^7$ to $10^9$ Lactobacillus bifidus microorganisms/g,
from 1 to 10 wt. % *Saccharomyces cerevisiae*,
from 0.05 to 0.3 wt. % retinol acetate,
from 1 to 3 wt. % D-alpha-tocopherol,
from 1 to 6 wt. % zinc and
from 2 to 20 wt. % oligofructose.

18. The method according to claim 16, wherein the composition is applied to an upper layer of the panty liner by a spraying process or one or more further layers are provided therewith.

19. The method according to claim 16, wherein the composition is activated by moisture.

20. The method according to claim 16, wherein the panty liner has a cover layer, a liquid-repelling layer, a storage layer and a backing layer.

21. The method according to claim 20, wherein the composition is contained solely in a layer directly beneath the cover layer of the panty liner.

22. The method according to claim 1, wherein the composition is administered in the form of a vaginal tampon.

23. The method according to claim 22, wherein the tampon contains from 2 to 4 g of the composition and the composition comprises:
from $10^7$ to $10^9$ Lactobacillus bifidus microorganisms/g,
from 1 to 10 wt. % *Saccharomyces cerevisiae*,
from 0.05 to 0.3 wt. % retinol acetate,
from 1 to 3 wt. %, D-alpha-tocopherol,
from 1 to 6 wt. % zinc,
from 1 to 5 wt. % *Melaleuca aetheroleum* or
from 2 to 20 wt. % oligofructose.

24. The method according to claim 22, wherein the tampon has a liquid-repellent outer layer and an inner storage layer.

25. The method according to claim 22, wherein the composition is applied to a superficial layer of the tampon by spraying or immersing processes or the composition penetrates the entire tampon.

26. The method according to claim 22, wherein the composition is contained solely in a layer directly beneath an outer cover layer of the tampon.

27. The method according to claim 22, wherein the composition is activated by moisture.

* * * * *